United States Patent [19]

Goldsberry

[11] Patent Number: Plant 6,663

[45] Date of Patent: Mar. 14, 1989

[54] DWARF CARNATION PLANT 'SNEFFELS'

[75] Inventor: Kenneth L. Goldsberry, Fort Collins, Colo.

[73] Assignee: Colorado State University Research Foundation, Fort Collins, Colo.

[21] Appl. No.: 71,806

[22] Filed: Jul. 10, 1987

[51] Int. Cl.[4] ..... A01H 5/00

[52] U.S. Cl. ..... Plt./71

[58] Field of Search ..... Plt./70–73

*Primary Examiner*—James R. Feyrer

*Attorney, Agent, or Firm*—Edwin L. Spangler, Jr.

[57] ABSTRACT

A carnation plant known by the cultivar name Sneffels was developed through a breeding program and is particularly characterized as to uniqueness by its dwarf growth habit and the following combined characteristics: upon pinching a rooted cutting, forms 3 to 4 lateral stems 21 to 27 cm long, each developing a terminal flower and 4 to 5 secondary buds which open intermittently as the terminal flowers seneses; lavender pink flowers 4.0 to 6.0 cm in diameter with a slight clove fragrance; can be grown under specified environmental conditions either as a single pinched plant per 10 cm pot or 3 pinched plants per 13 cm pot, which results in an ideal new flowering house plant.

1 Drawing Sheet

My present invention relates to a new and distinct dwarf cultivar of *Dianthus caryophyllus* Linn. identified as plant 85-215-98 and given the name Sneffels.

Sneffels is a product of a breeding program started by me at Colorado State University in 1974, using commercially available semi dwarf germplasm, crossing selected unnamed seedlings and incorporating various known carnation germplasm with an objective of creating dwarf carnation cultivars that could be asexually produced for commercial use, in controlled environments, as flowering house plants.

Sneffels was originated from a cross made in a controlled breeding program at the Horticulture Department, W. D. Holley Plant Environmental Research Center, Colorado State University, Fort Collins, Colo. using the unnamed seed parent 83-15-20 and an unnamed pollen parent 82-43A, also developed by the present inventor.

Sneffels was discovered and selected as one flowering plant within the progeny of the stated cross by Kenneth L. Goldsberry on May 23, 1983 in a controlled environment in Fort Collins, Colo.

The first act of asexual reproduction of Sneffels was accomplished when vegetative cuttings were taken, by the inventor, from the initial selection on Sept. 15, 1983 in a controlled environment in Fort Collins, Colo. The initial rooting of the cuttings and performance of the resulting plants have demonstrated that the distinctive characteristics of this new cultivar Sneffels, herein disclosed, appear to be firmly fixed and hold true from generation to generation.

Sneffels has not been observed under all possible environmental conditions. The phenotype may vary significantly with variation in the production environment including irrigation regimes, temperature, light intensity, day length and nutritional programs. It has been observed and evaluated, from a rooted cutting to a mature plant while being grown in Fort Collins and Denver, Colo. and Encintias and Salinas, Calif. under greenhouse conditions, which approximate those generally used in commercial practice.

The following traits, which have been repeatedly observed, characterize Sneffels and distinguishes it as a new and distinct dwarf carnation cultivar:

1. Somatic chromosome is 2n=30
2. A double type flower, similar to commercial cut flower spray types
3. Flower sizes range from 4.0 to 6.0 cm in diameter
4. Lavender pink flower color
5. Late flowering response on a scale of early, medium or late flowering
6. Three to four lateral shoots develop following a pinch of the main stem.
7. The terminal flower, four to five secondary buds and some tertiary buds form on each flowering stem. As the old flowers senese, the secondary buds continue to open, the tertiary buds usually abort
8. Secondary peduncle lengths on a single stem varies between 1.2 to 18.2 cm
9. Plant height ranges between 21.0 to 27.0 cm
10. Has a distinct clove fragrance There are no dwarf carnation cultivars, for house plant use, presently developed and known to the inventor.

BRIEF DESCRIPTION OF THE DRAWING

The accompanying top colored photograph taken on May 1, 1987, using an 18 percent Kodak photographic gray card as a color base, illustrates in perspective view and the overall appearance of Sneffels (83-40-2) grown in 10 cm (single plant) and 15 cm (3plants) azalea pots. The bottom photo shows buds, inflorescence, stem, foliage characteristics and color of Sneffels are typical and true as possible with illustrations of this type.

The following detailed description of my new dwarf carnation cultivar are based upon observations of greenhouse grown plants made in 1986 at 1987 at Fort Collins, Colo. The color values were determined in a standard color viewing booth with a 5000° K. fluorescent light source using references developed and published by The Royal Horticultural Society, London, England.

PLANT CHARACTERISTICS

Origin: Seedling selection.

Parentage:

*Seed parent.*—Selected unnamed seedling, 80-5B (Goldsberry).

*Pollen parent.*—Selected unnamed seedling 77-27 (Goldsberry).

Classification:

*Botanic* —*Dianthus caryophyllus* Linn. cv. Sneffels.

*Commercial.*—Dwarf carnation for pot plant production.

Propagation: Vegetative cuttings, 6 to 8 cm. in length initiate visible roots in 8 to 10 days in the winter and 5 to 8 during the summer, when rooted under mist in a rooting medium temperature of 20° C. A quality rooted cutting with an abundance of roots, is usually ready to plant in 15 days in the summer and 18 to 20 in the winter.

Growth habit: Three to four lateral shoots form naturally, but are accelerated by removing the terminal portion of the main stem, at the sixth or seventh node from the top, resulting in a compact, bushy and strong upright plant. Some basal branches may elongate enough to place apical buds on a plane equal to the terminal flowers of the initial stems.

Stems: Numerous lateral branches form close to the base of the plant and vary in length from 21–27 cm, having 8 to 11 nodes with opposite leaves. A reproductive bud usually forms at each upper 4 to 6 nodes. Shoots forming at the seventh or eleventh node below the terminal flower, usually develop into another flower stem in proper environmental conditions. All stems have a blue-grey glaucous condition, approximating 189B in color.

Foliage: Leaves are abundant and typical of the commercial carnation type. The leaves at the seventh node from the top of each stem range in length from 9.7 to 12.7 cm. The widest leaf widths are present on nodes 4 or 5 and vary from 1.0 to 1.4 cm. The foliage is progressively smaller above and below these nodes. Both the upper and lower sides of the leaves are dark green and have a blue-grey glaucous condition. The color of both surfaces is identified as 189B with the surface bloom present and 137A when it is removed.

INFLORESCENCE CHARACTERISTICS

Buds: Terminal buds average 2.6 cm in length just prior to opening and the secondary buds 2.0 to 2.6 cm. The average bud circumference ranges from 5.7 cm for the terminal and 4.5 cm. for secondary buds, at the first sign of petal color. Secondary buds tend to form in the axil of both leaves at the second and third nodes below the terminal flower. Secondary buds often do not form in the axil of the first node below the terminal flower. Significantly visible tertiary buds form on the peduncles of the upper four secondary buds, but normally do not open in low light conditions. Buds are oval in shape and pointed.

Sequence of development: The terminal bud on each stem will show color before any lateral bud color is visible. The opening sequence of the secondary buds is generally at node positions one, two, three and six from the terminal flower position on each stem. In the proper environments, new flower bearing shoots emerge from the eighth to eleventh nodes below the terminal flower and at the base of the plant, creating a perpetual flowering plant in high light conditions.

Flowering response: A rooted cutting pinched 1 to 2 weeks after planting will flower 15 to 17 weeks following the pinch from a October 1 plant date and 12 to 14 weeks from a June 1 date in Fort Collins, Colo. when growing temperatures approximate 11° C. at night and 17° C. during the day.

Inflorescence type: Each initial stem is a semi-compound spray with a terminal bud, 4 to 5 secondary and 3 to 5 lateral shoots.

Number of buds and flowers per stem: Each stem has a terminal flower that develops along with the upper most, of the 5 to 6 secondary buds; new flowering shoots usually form at the seventh to eleventh nodes of each initial stem resulting in an average of 5.0 flowers per stem. The tertiary buds do not develop petals in low light and remain small, not opening.

Peduncle length: The length of the peduncles range from 1.8 cm for the top secondary bud to 18.2 cm for the lowest bud, on each stem, when the terminal flower is in prime condition. The peduncles of the tertiary buds vary from 0.2 to 0.4 cm.

Peduncle stength: Strong, holds flowers erect during all growing seasons; degree of brittleness is related to environmental conditions.

Flower:

*Size.*—Terminal flowers range in size from 4.0 to 6.0 cm and the secondaries, 4.0 to 5.0 cm depending on the environment.

*Type.*—Commercial double with 60 to 90 highly serrated petals in the terminal flowers, which have an average length and width of 4.1 cm and 2.3 cm, respectively.

*Form.*—Sub hemispherical in longitudinal section with the petals adjacent to the calyx, slightly reflexed at maturity. Seldom splits. The secondary flowers are 4.0–5.0 cm in diameter and have an average of 55 petals 3.6 cm long and 2.0 cm wide. The secondary flowers split periodically.

Corolla color: General tonality at a distance of 1 meter: 69B at petal margins. Upper petal surface: newly opened petals are 69B in color, but fade to 69A in greenhouse conditions. Lower petal surface: have the same color characteristics as the upper surface.

Keeping quality: In the greenhouse, individual flowers remain aesthetically pleasing up to 6 days; in the home 6 to 12 days with room temperatures of 17° C. and high, natural light intensity.

Fragrance: Clove fragrance which increases with temperature.

Reproductive organs:

*Androecium.*—Typical carnation except has 26–40 filaments, few anthers and no pollen.

*Gynoecium.*—Typical of carnation in all respects; pistil is 1.0 to 1.3 cm in length, grooved and has 2 styles and stigmas. The stigmas are white at all stages of maturity.

Disease resistance: The plant has been found free of pathogen races currently associated with standard carnation cultivars, including the wilts and Etched Ring or Fleck viruses.

I claim:

1. A new and distinct cultivar of *Dianthus caryophyllus,* Linn, identified as 83-40-2 and known as Sneffels and substantially as herein described and illustrated.

* * * * *

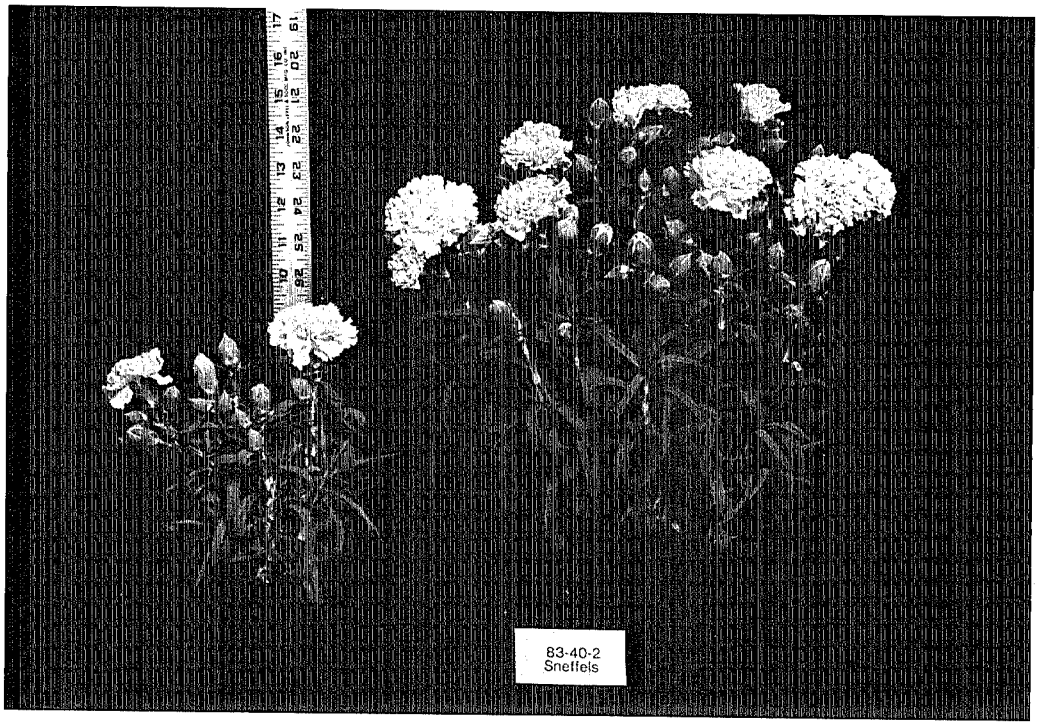
83-40-2
Sneffels
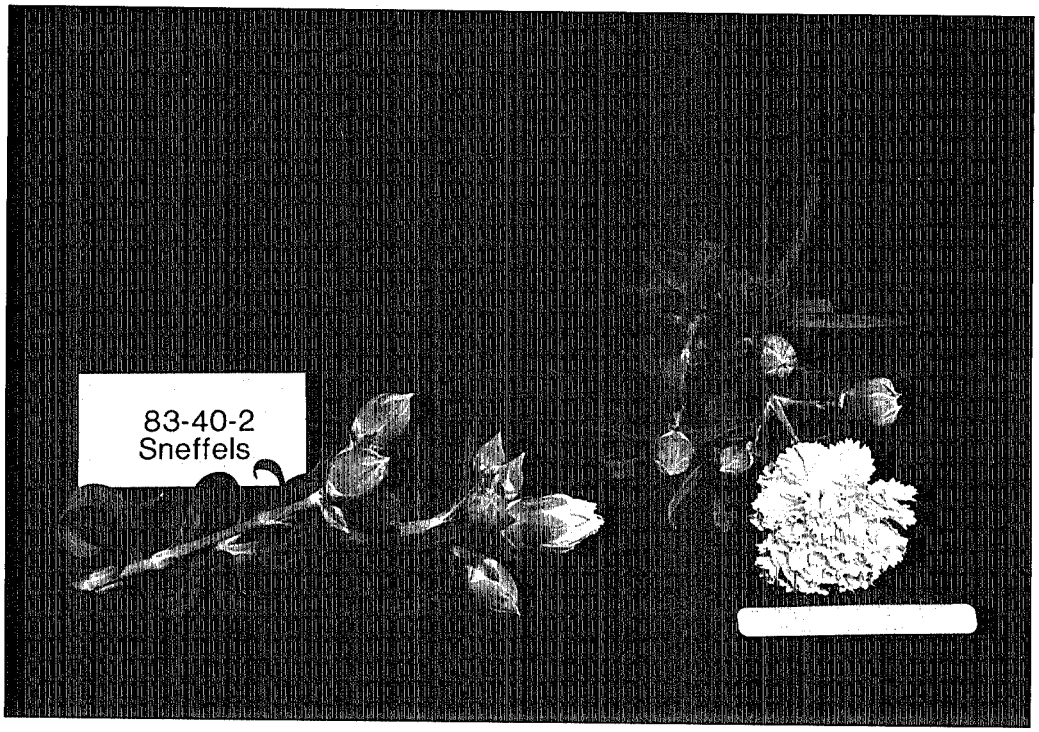
83-40-2
Sneffels